US008532951B2

(12) United States Patent
Roy et al.

(10) Patent No.: US 8,532,951 B2
(45) Date of Patent: Sep. 10, 2013

(54) METHOD FOR CALIBRATING A TRANSDUCER ARRAY

(75) Inventors: Olivier Roy, Royal Oak, MI (US); Neb Duric, Bloomfield Hills, MI (US); Ivana Jovanovic, Lausanne (CH); Martin Vetterli, Grandvaux (CH)

(73) Assignee: Delphinus Medical Technologies, Inc., Plymouth, MI (US)

( * ) Notice: Subject to any disclaimer, the term of this patent is extended or adjusted under 35 U.S.C. 154(b) by 343 days.

(21) Appl. No.: 12/976,462

(22) Filed: Dec. 22, 2010

(65) Prior Publication Data

US 2011/0146371 A1    Jun. 23, 2011

Related U.S. Application Data

(60) Provisional application No. 61/289,154, filed on Dec. 22, 2009.

(51) Int. Cl.
| | |
|---|---|
| G01D 18/00 | (2006.01) |
| G01D 21/00 | (2006.01) |
| G01P 21/00 | (2006.01) |
| G01R 35/00 | (2006.01) |
| G01B 3/30 | (2006.01) |
| G01B 21/00 | (2006.01) |

(52) U.S. Cl.
USPC ............................................. 702/85; 73/1.79

(58) Field of Classification Search
USPC .................... 702/85; 600/447, 459; 73/1.79
See application file for complete search history.

(56) References Cited

U.S. PATENT DOCUMENTS

2002/0120196 A1 *  8/2002  Dubberstein et al. ......... 600/447

OTHER PUBLICATIONS

C. H. Knapp and G. C. Carter, "The generalized correlation method for estimation of time delay," IEEE Transactions on Acoustics, Speech and Signal Processing, vol. 24, No. 4, pp. 320-327, Apr. 1976.
P. Drineas, A. Javed, M. Magdon-Ismail, G. Pandurangant, R. Virrankoski, and A. Savvides, "Distance matrix reconstruction from imcomplete distance information for sensor network localization" 3rd Annual IEEE Communications Society on Sensor and Ad Hoc Communications and Networks, Sep. 2006, pp. 536-544.
J. A. Cadzow, "Signal enhancement—A composite property mapping algorithm," IEEE Transactions on Acoustics, Speech and Signal Processing, vol. 36, No. 1, pp. 49-62, Jan. 1988.

* cited by examiner

*Primary Examiner* — Alexander H Taningco
*Assistant Examiner* — Manuel Rivera Vargas
(74) *Attorney, Agent, or Firm* — Jeffrey Schox

(57) ABSTRACT

An iterative method for calibrating a transducer array characterized by calibration parameters, based on time delay measurements between transducer pairs, comprising the steps of: creating a distance data set that includes pairwise distances between estimated positions of transducer; forming a time delay measurement data set that includes time delay measurements between transducer pairs; generating from the time delay measurement data set an estimate of at least one calibration parameter; modifying the time delay measurement data set and the distance data set based on the estimated calibration parameters; denoising the modified distance data set with an iterative algorithm; updating the estimated positions of transducers based on the denoised modified distance data set; and repeating at least a portion of the steps until the difference between the estimated positions of transducer pairs and updated estimated positions of transducers satisfies a stopping criterion.

38 Claims, 8 Drawing Sheets

FIGURE 7
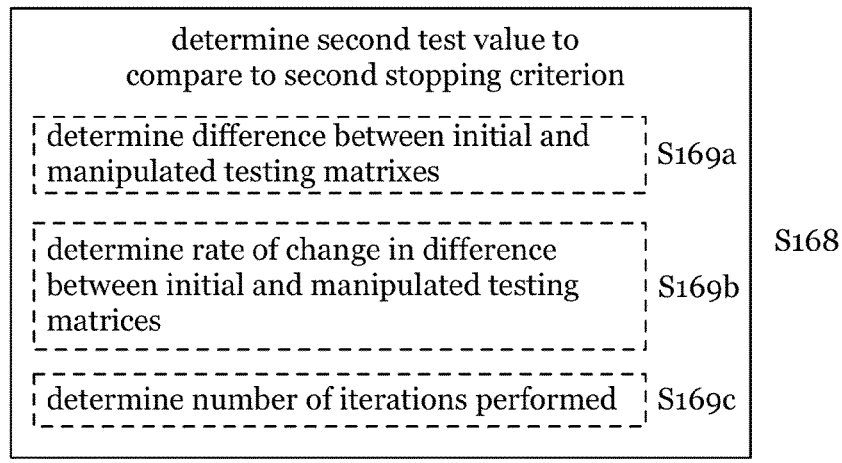
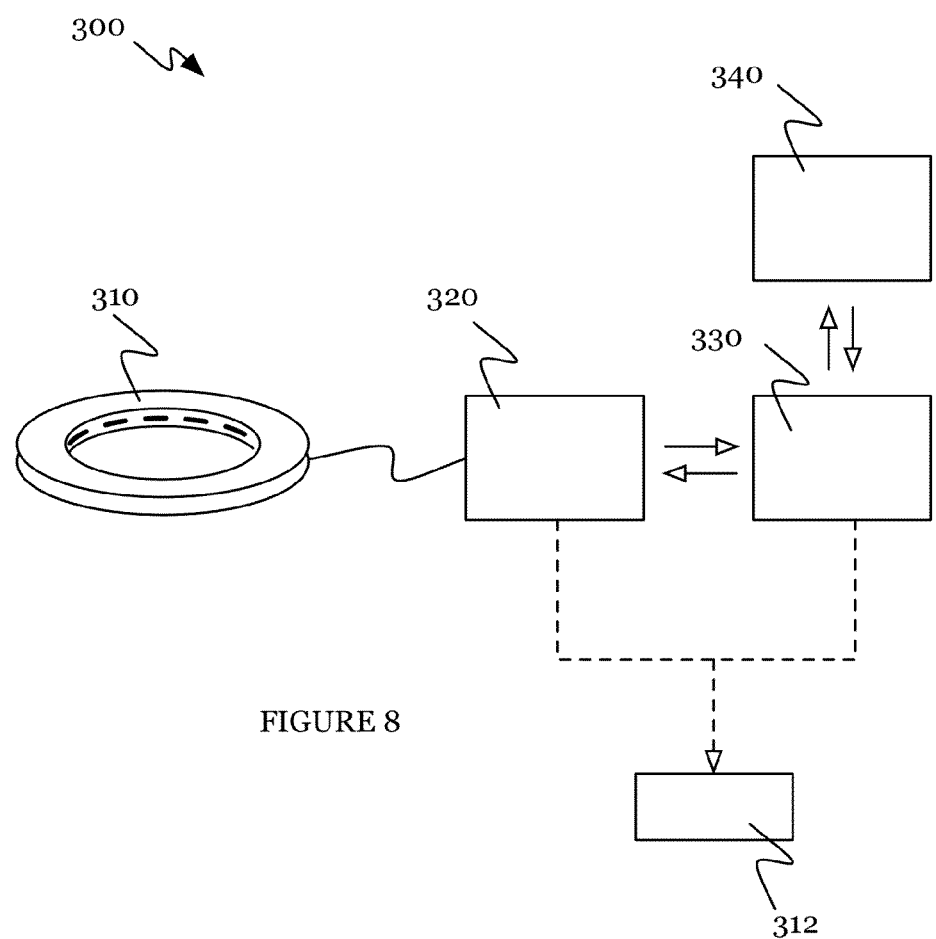
FIGURE 8

METHOD FOR CALIBRATING A TRANSDUCER ARRAY

CROSS-REFERENCE TO RELATED APPLICATIONS

This application claims the benefit of U.S. Provisional Application No. 61/289,154, filed on 22 Dec. 2009, which is incorporated in its entirety by this reference.

TECHNICAL FIELD

This invention relates generally to the transducer field, and more specifically to an improved method for calibrating a transducer array.

BACKGROUND

In an array of transducers that emit and/or receive signals, each transducer may be characterized by a number of parameters that affect overall measurements of signals passed among the transducers, and the processing of such signals. For instance, in an array of N transducers having positions denoted as $x_i$ (i=0, 1, ..., N−1), each transducer may be assumed to have unknown but fixed emission and reception delays (denoted by $e_i$ and $r_i$, respectively). These and other calibration parameters affect overall time delay measurement $m_{i,j}$, or the time elapsed between when a probing signal sent to an emitter and when a signal is recorded at a receiver. In various applications of transducer arrays, the accuracy of acquired data and the processing of such data rely on accurate estimates through calibration parameters characterizing the transducers. However, in practice when calibrating transducer arrays using time delay measurements, only a noisy version of these time delay measurements $m_{i,j}$ (i.e., $\hat{m}_{i,j}$) is obtainable or accessible. The origin of the noise is manifold, but includes electronic noise, non-ideal sensor characteristics and in-homogeneities in the propagation medium. The measurement $\hat{m}_{i,j}$ can also be considered as missing when, for example, the signal-to-noise ratio of the output signal is too weak to provide a relevant estimate, or if any transducers are faulty, thereby leading to a faulty time delay measurement. These and other complications typically inhibit accurate and robust calibration of the transducer array. Thus, there is a need in the transducer field to create an improved method for calibrating a transducer array using time delay measurements. This invention provides such an improved method for calibrating a transducer array.

BRIEF DESCRIPTION OF THE FIGURES

FIG. 7 is a detailed schematic of the step of determining a test value to compare to a second stopping criterion in the method of a preferred embodiment;

FIG. 8 is a schematic of the system for calibrating a transducer array of a preferred embodiment;

DESCRIPTION OF THE PREFERRED EMBODIMENTS

The following description of preferred embodiments of the invention is not intended to limit the invention to these preferred embodiments, but rather to enable any person skilled in the art to make and use this invention.

Figure 1:
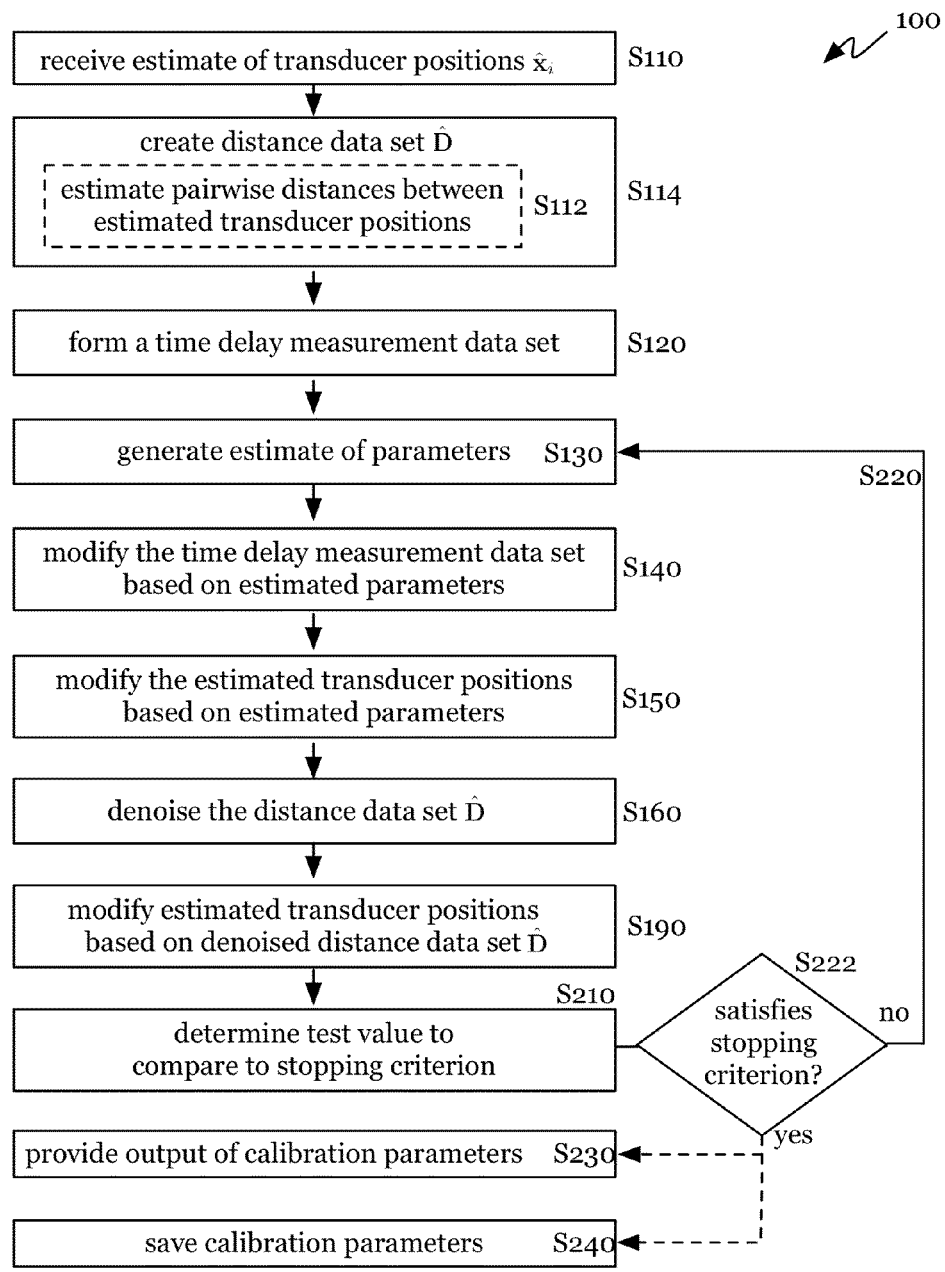
FIG. 1 is a schematic of the method for calibrating a transducer array of a preferred embodiment.

In a preferred embodiment, as shown in FIG. 1, the method 100 for calibrating a transducer array characterized by calibration parameters, based on time delay measurements between transducer pairs, includes the steps of: receiving an estimate of the positions of the transducers S110; forming a time delay measurement data set S120 that includes time delay measurements between transducer pairs, including non-faulty time delay measurements and any faulty time delay measurements; generating from the time delay measurement data set an estimate of at least one calibration parameter S130; modifying the time delay measurement data set S140 including modifying the faulty time delay measurements, based on the estimated calibration parameters; modifying the estimated positions of the transducers S150 based on the estimated calibration parameters; determining a test value for comparing to a stopping criterion S210; and step S220, which includes repeating steps S130 through S210 until a stopping criterion is met. The method 100 may further include the step of denoising a distance data set or testing matrix S160 representing the modified estimated positions of the transducers, and modifying estimated transducer positions based on the denoised distance data set S190. The method 100 preferably further includes providing an output of at least one modified estimated calibration parameters S230 and/or storing at least one of the modified estimated calibration parameters S240. In one preferred embodiment, the method stores or provides an output of estimates of one or more of the following calibration parameters: respective emission delays for each transducer in the transducer array, respective reception delays for each transducer in the transducer array, positions of the transducers in the transducer array (relative and/or absolute), and speed of signal propagation. The emission, reception, and/or transducer positions may be presented, for example, in the form of a vector or a table. The method 100 provides an accurate and robust array calibration using time delay measurements, using an iterative masking approach to recover missing or faulty data obtained for calibration. The time delay measurements are preferably obtained through a test operation of the transducer array, but may alternatively be retrieved from storage, received from a user, and/or received in any suitable manner. The method 100 is also robust to noise and model mismatch, including a unique iterative denoising algorithm to further improving accuracy of the calibration.

The method 100 is used to calibrate an array of transducers, preferably for an array of ultrasound transducers, but may be used to calibrate any suitable kind of transducers in any suitable arrangement. The transducer array is preferably used to propagate signals in a presumably homogeneous environment (with constant but unknown speed of signal propagation), but may alternatively be used in any suitable environment. In an array of N transducers with emit and receive capabilities, the position of transducer i may be denoted by $x_i$ for (i=0, 1, . . . , N−1) and each transducer may be assumed to have unknown but fixed emission and reception delays (denoted by $e_i$ and $r_i$, respectively, with delay vectors e and r whose ith component is respectively given by $e_i$ and $r_i$). These parameters affect overall time delay measurement $m_{i,j}$, or the time elapsed between when a probing signal sent to a transmitter and when a signal is recorded at a receiver. This delay can be decomposed as $$m_{i,j} = t_{i,j} + e_i + r_j \quad (1)$$

where $t_{i,j}$ denotes the actual propagation time between transducers i and j, also referred to as "time of flight". The signals are assumed to propagate in an homogeneous environment with unknown propagation speed c. Hence, the time of flight $t_{i,j}$ satisfies $$d_{i,j} = c t_{i,j} \quad (2)$$

where $d_{i,j} = \|x_i - x_j\|$ is the Euclidean distance between transducers i and j. A time of flight matrix T may be defined with $(T)_{i,j} = t_{i,j}$, a distance matrix D may be defined with $(D)_{i,j} = d_{i,j}$, and a time delay measurement matrix M may be defined with $(M)_{i,j} = m_{i,j}$. In this manner, the distance matrix only depends on the position of the sensors $x_i$ and that D=cT. Estimated or noisy versions of these quantities are denoted with a hat symbol (e.g., $\hat{M}$). In one preferred embodiment in the context of these definitions, the method 100 aims to find one or more of the calibration parameters $\hat{c}, \hat{e}, \hat{r}$ and $\hat{x}_i$ that best fit the measurements in a mean square sense. More precisely, the method may solve the optimization problem of:

$$\min_{c,e,r,x_i} \|M - \hat{M}\|^2 = \min_{c,e,r,x_i} \|c^{-1}D + e1^T + 1r^T - \hat{M}\|^2, \quad (3)$$

where 1 denotes the all-one vector and the dependency of the matrix D on the positions $x_i$ is implicit. The equality in (3) follows directly from (1) and (2).

Step S110, which includes receiving an estimate of the positions of the transducers, functions to establish an initial set of positions of the transducers for the iterative algorithm. The manner in which the positions of the transducers quantitatively represent the transducer arrangement may depend on the particular nature of the arrangement. In one variation, the positions of transducers in a transducer array may be quantified relative to one or more known reference points. In another variation, the positions of transducers in a transducer array may be quantified by the position between adjacent or consecutive transducer elements. For example, for a ring transducer having transducer elements arranged circumferentially around a ring, the positions of the transducer elements may be quantified by the distance of each transducer element to the center of the ring, and/or quantified by the angle between adjacent transducer elements. In another example, for a linear array of transducer elements, the positions of the transducer elements may be quantified by the distance of each transducer from one end of the linear array. However, the estimated positions of the transducers may be quantified in any suitable manner.

In an array of N transducers with emit and receive capabilities, the position of transducer i may be denoted by $\hat{x}_i$ for (i=0, 1, . . . , N−1). Receiving an estimate of the positions of the transducers may include estimating the pairwise Euclidean distances S112 between estimated positions of transducers (denoted by $d_{i,j} = \|x_i - x_j\|$ as the Euclidean distance between transducers i and j), and creating a distance matrix $\hat{D}$ S114 of estimated pairwise distances between estimated positions of transducers (denoted by $(D)_{i,j} = d_{i,j}$). However, the estimated positions of transducers may be represented in any suitable distance data set or other manner. The method may further include storing the estimated positions of the transducers as a current set of estimated transducer positions $\hat{x}_i$. The received estimated positions of transducers may be previously stored, received as input from a user, transferred from a storage unit, and/or be received in any suitable manner. Alternatively, the method may further include the step of estimating the positions of the transducers, such as by analyzing a photograph or other representation of the transducers or deriving from one or more previous estimates of the positions of the transducers (e.g., by averaging multiple sets of prior estimates).

Figure 2:
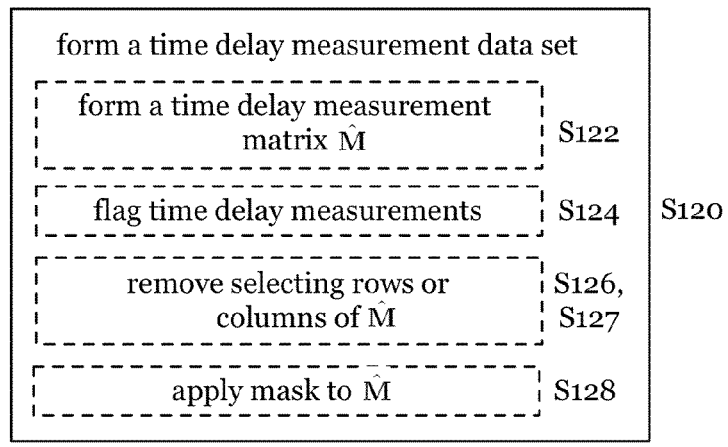
FIG. 2 is a detailed schematic of the step of forming a time delay measurement data set in the method of a preferred embodiment.

Step S120, which includes forming a time delay measurement data set, functions to contain measured and/or estimated values of time delay measurements $m_{i,j}$. The time delay measurement data set preferably includes non-faulty time delay measurements and faulty time delay measurements (e.g., due to high noise, faulty or missing transducers, etc.). As shown in FIG. 2, forming a time delay measurement data set S120 preferably includes forming a time delay measurement matrix M of the time delay measurements S122, with $(M)_{i,j} = m_{i,j}$. Step S120 preferably further includes flagging faulty time delay measurements S124, which may be suspicious due to their value relative to adjacent time delay measurements, known faults in particular transducers, and/or any suitable reason. Any other non-faulty time delay measurements may additionally and/or alternatively be flagged. In one variation, flagging faulty time delay measurements S124 includes one or more of the following steps: removing selected rows of the time delay measurement matrix $\hat{M}$ (such as those corresponding to faulty transducers) S126, removing selected columns of the time delay measurement matrix M S127, and applying a mask to the time delay measurement matrix $\hat{M}$ S128 that sets the missing time delay measurements to zero. However, flagging faulty time delay measurements S124 may additionally and/or alternatively include setting selected rows or columns to an alternative suitable value, or any suitable flagging step.

Step S130, which includes generating from the time delay measurement data set an estimate of at least one calibration parameter, functions to find values for at least one calibration parameter that best fit the time delay measurement data set or matrix. Generating an estimate of at least one calibration parameter S130 preferably includes optimizing values for at least one calibration parameter using the non-faulty time delay measurements. The estimates of the optimized calibration parameters are preferably obtained using non-faulty time delay measurements, but may incorporate the faulty time delay measurements in some manner (e.g., weighing the importance of the non-faulty measurements greater than the faulty measurements). In a preferred embodiment, optimizing values for at least one calibration parameter includes computing mean square estimates of at least one calibration parameter. For example, optimizing values for at least one calibration parameter involves computing the mean square optimal estimates of the speed of signal propagation ĉ, as well as the emission and reception delays denoted ê and r̂, using the non-zero elements of M̂. Step S130 preferably solves the optimization problem of (3) using the non-zero elements of M̂.

The optimization of (3) may also be written as:

$$\|c^{-1}D + e1^T + 1r^T - \hat{M}\|^2 = \|vecc^{-1}D + vece1^T + vec1r^T - vec\hat{M}\|^2 \quad (4)$$
$$= \|c^{-1}d + K_e e + K_r r - \hat{m}\|^2,$$

where d=vecD and m̂=vecM̂ are vectors obtained by stacking the columns of D and M̂, respectively. The matrices $K_e$ and $K_r$ are given by $$K_e = 1 \otimes I = \begin{bmatrix} I \\ I \\ \vdots \\ I \end{bmatrix}$$

and $$K_r = I \otimes 1 = \begin{bmatrix} 1 & 0 & \cdots & 0 \\ 0 & 1 & \cdots & 0 \\ \vdots & \vdots & \ddots & \vdots \\ 0 & 0 & \cdots & 1 \end{bmatrix}$$

where $\otimes$ denotes the Kronecker product and I the identity matrix. Defining the matrix K and the vector p as $$K = \begin{bmatrix} I & K_e & K_r \end{bmatrix}$$

and $$p = \begin{bmatrix} d/c \\ e \\ r \end{bmatrix},$$

respectively, the optimization problem (3) can be expressed as $$\min_{c,e,r,x_i} \|Kp - \hat{m}\|^2. \quad (5)$$

The above optimization depends on the positions of the transducers only through the distance vector d. The vector d is invariant with respect to translation, rotation and symmetry of the transducers; therefore the positions derived from d can be relative, but absolute positioning can easily be obtained by specifying a few references (e.g., the center of the array, the position of a reference transducer). The minimization (5) can be thus be carried in terms of this vector instead of the individual positions, that is, $$\min_{c,e,r,d} \|Kp - \hat{m}\|^2. \quad (6)$$

Optimal values ĉ and d̂ can only be determined up to a positive scaling factor, as apparent from the definition of the vector p.

The solution to the minimization (6) is obtained by orthogonal projection as $$\hat{p} = K^\setminus \hat{m}, \quad (7)$$

where $K^\setminus$ is the Moore-Penrose pseudoinverse given by $K^\setminus = K^T(KK^T)^{(-1)}$ in the full rank. Given an estimate of the propagation speed ĉ, the estimated delay vectors ê and r̂ can be retrieved from p̂.

Figure 3:
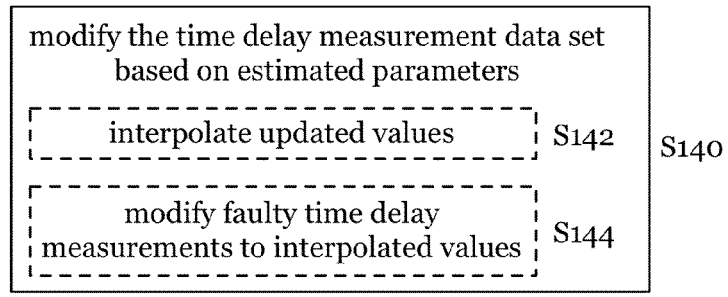
FIG. 3 is a detailed schematic of the step of modifying the time delay measurement data set in the method of a preferred embodiment.

Step S140, which includes modifying the time delay measurement data set, functions to modify faulty time delay measurements using the estimated calibration parameters. As shown in FIG. 3, modifying the time delay measurement data set preferably includes interpolating updated values for the faulty time delay measurements S142 using estimated calibration parameters and modifying the faulty time delay measurements to the interpolated values S144. In a preferred embodiment, interpolating updated values includes interpolating updated values based on the current estimated positions of the transducers (e.g., relative positions in the distance matrix D̂) and an estimated speed of propagation obtained in step S130. Any suitable method of interpolation may be used; several methods of interpolation are familiar to one ordinarily skilled in the art.

Figure 4:
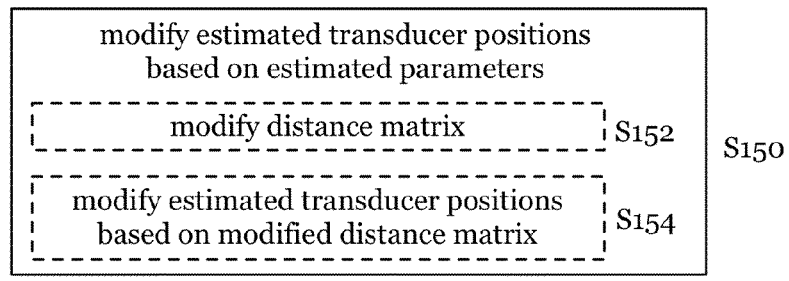
FIG. 4 is a detailed schematic of the step of modifying estimated positions of transducers in the method of a preferred embodiment.

Step S150, which includes modifying the estimated positions of the transducers based on the estimated calibration parameters, functions to update the estimated transducer positions as part of a successive iteration as necessary in the method 100. Modifying the estimated positions of the transducers S150 may include modifying the estimated relative positions based on estimated values of at least emission and reception delay parameters $e_i$ and $r_i$. In particular, as shown in FIG. 4, modifying the estimated positions of the transducers S150 preferably includes modifying the distance matrix D̂ S152. In one variation, modifying the estimated positions of the transducers S150 further includes modifying the estimated positions of the transducers $\hat{x}_i$ based on the modified distance matrix S154. In another variation, the method may further include denoising the modified distance matrix S160 and modifying the estimated positions of the transducers based on the denoised modified distance set S210 (e.g., modifying the estimated positions of the transducers based on the modified distance matrix S154 without denoising the modified distance matrix). In yet another variation, the method may include modifying the estimated positions of the transducers based on the modified distance matrix S154, denoising the modified distance matrix S160, and modifying the estimated positions of the transducers based on the denoised modified distance data set S210, such as to compare the effect of denoising the modified distance data set).

Modifying the distance matrix D̂ S152 may include subtracting estimated emission and reception delay values $e_i$ and $r_i$ from the time delay measurement matrix and multiplying the result of the subtraction by the estimated speed of propagation ĉ. However, the distance matrix D̂ may additionally and/or alternatively include any suitable steps for modification. In particular, based on the initial estimate $d_0$ of the distance vector, the modifying step S152 may solve the optimization problem $$\min_{c,e,r} \|Kp - \hat{m}\|^2, \quad (8)$$

where the matrix K and the vector p are now defined as $$K = [\, d_0 \quad K_e \quad K_r \,]$$

and $$p = \begin{bmatrix} 1/c \\ e \\ r \end{bmatrix},$$

respectively. The estimated sound speed $\hat{c}$ and delay vectors $\hat{e}$ and $\hat{s}$ can be retrieved from $\hat{p}$ computed using (7), and the distance vector $\hat{d}$ can further be estimated as $$\hat{d} = \hat{c}(\hat{m} - K_e \hat{e} - K_r \hat{r}). \tag{9}$$

Denoising the modified distance matrix S160 may include storing a testing matrix that represents elements in the modified distance matrix and iteratively reinforcing at least one desired property of the testing matrix. In the method 100, denoising the modified distance matrix S160 cleans the distance matrix obtained in (9) prior to modifying the estimated positions of the transducers based on the denoised modified distance matrix. The denoising step S160 reduces the effect of the noise on calibration accuracy and hence permits the use of relatively cheap, possibly off-the-shelf electronic components in or in conjunction with the transducer array. In one variation, the testing matrix preferably includes the square of every element in the modified distance matrix $\hat{D}$. In another variation, the testing matrix includes the square of every element in a time-of-flight matrix defined as $T = c^{-1} D$. The reinforced properties of the testing matrix are preferably at least one of matrix symmetry, zero diagonal elements, non-negative elements, and rank equal to or less than four, although any other suitable properties may additionally and/or alternatively be reinforced.

Figure 6:
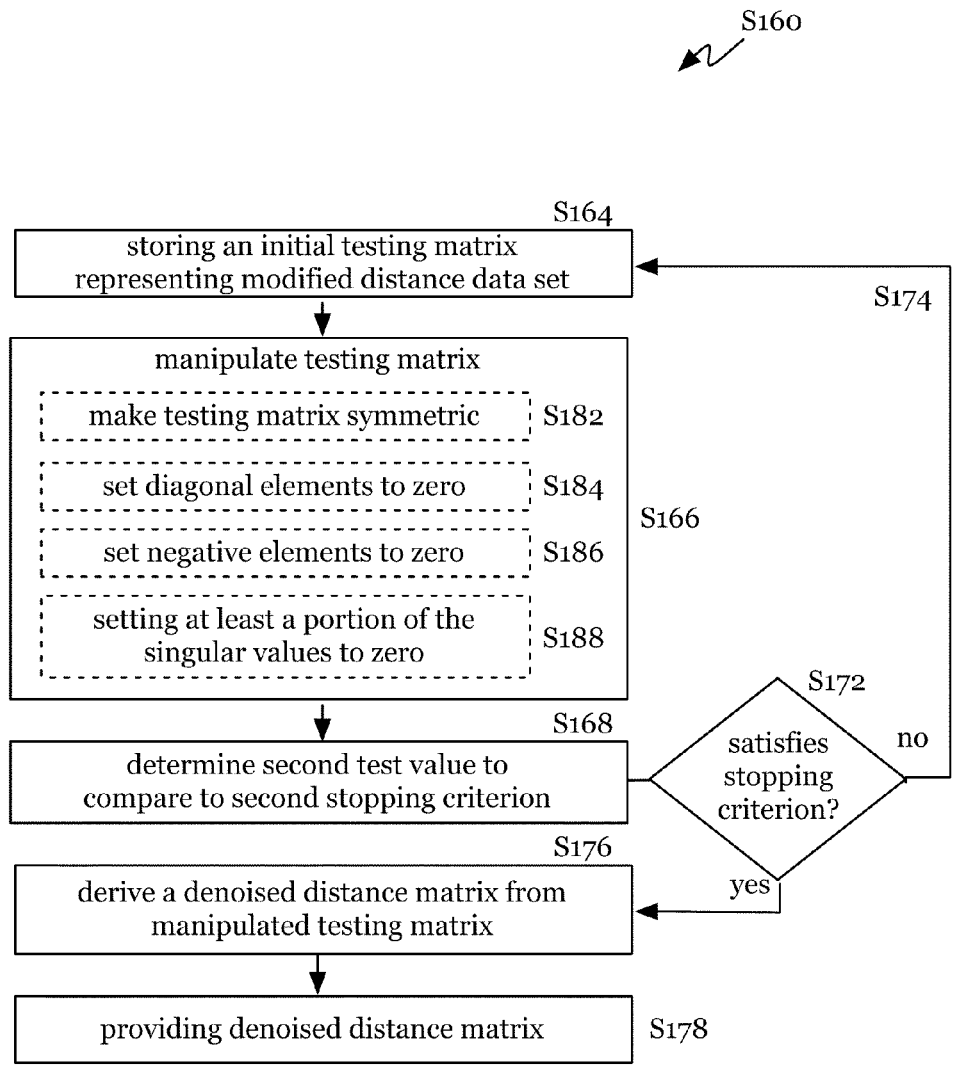
FIG. 6 is a detailed schematic of the step of denoising the distance data set in the method of a preferred embodiment.

As shown in FIG. 6, denoising the modified distance matrix $\hat{D}$ S160 preferably includes storing an initial testing matrix Q S164, manipulating the initial testing matrix Q to possess at least one desired property S166, determining a test value to compare to a second stopping criterion S168 (separate from the stopping criterion in the higher-level calibrating method 100), and repeating the steps of storing, manipulating, and determining a test value S174 until the second stopping criterion is met. In each iteration the repeated step of storing an initial matrix includes storing an initial testing matrix that is equivalent to the manipulated testing matrix of the previous iteration.

In a more detailed preferred embodiment, the step of denoising S160 manipulates a testing matrix Q to reinforce the following key properties:

1. Q is symmetric, i.e., $Q = Q^T$.
2. Q has zero diagonal elements, i.e., $(Q)_{i,i} = 0$ for $i = 0, 1, \ldots, N-1$.
3. Q has non-negative elements, i.e., $(Q)_{i,j} \geq 0$ for $i,j = 0, 1, \ldots, N-1$.
4. Q is of rank at most 4, i.e., rank $Q \leq 4$.

The property of rank of most four can easily be shown by one ordinarily skilled in the art. Due to the presence of noise in the measurements, the matrix Q obtained by squaring every elements of the distance matrix $\hat{D}$ estimated using (9) will fail to have some of these properties. The key idea is to successively enforce these properties as a means to denoise $\hat{D}$. This is achieved by means of the following mappings:

1. $\phi_1(Q) = (\tfrac{1}{2})(Q + Q^T)$.
2. $\phi_2(Q)$ sets the diagonal elements of Q to zero.
3. $\phi_3(Q)$ sets the negative elements of Q to zero.
4. $\phi_4(Q)$ sets the N−4 smallest singular values of Q to zero.

It can be shown that the sequence of matrices obtained by iteratively applying the above mappings converges, in the limit of a large number of iterations, to a matrix that possesses the four required properties (see, e.g., J. A. Cadzow, "Signal enhancement—A composite property mapping algorithm," *IEEE Transactions on Acoustics, Speech and Signal Processing*, vol. 36, no. 1, pp. 49-62, January 1988, which is incorporated in its entirety by this reference). Note that symmetry is not violated by any of the mappings. Hence, it just needs to be enforced at the beginning of the iterations.

As shown in FIG. 7, determining a test value to compare to a second stopping criterion S168 may be one or more of several variations. In a first variation, determining a test value S168 includes determining the difference between the initial and manipulated testing matrices Q and Q' S169a. In a second variation, determining a test value S168 includes determining the rate of change in the difference S169b between the initial and manipulated testing matrices between subsequent iterations. In a third variation, determining a test value S168 includes determining the number of iterations S169c that have been performed in the current denoising step of method 100. The repeating step S174 then checks whether this test value satisfies a second stopping criterion (e.g., threshold in difference, threshold in rate in change of difference, predetermined number of iterations). However, determining a test value S168 may include any suitable steps to determine any suitable test value for comparing any suitable stopping criterion.

This procedure, as exemplified in one preferred embodiment, is summarized below:

Distance Matrix Denoising
Input: A noisy distance matrix $\hat{D}$.
Output: A cleaned distance matrix D.
Procedure:
1. Compute $\hat{Q}_1 = \phi_1(\hat{Q})$, where $\hat{Q}$ is obtained by squaring every element of $\hat{D}$.
2. Compute $\hat{Q}_2 = \phi_2(\hat{Q}_1)$.
3. Compute $\hat{Q}_3 = \phi_3(\hat{Q}_2)$.
4. Compute $\hat{Q}_4 = \phi_4(\hat{Q}_3)$.
5. If the norm of the difference $\|\hat{Q}_4 - \hat{Q}_1\| > \delta$ for some prescribed threshold $\delta$, set $\hat{Q}_1 = \hat{Q}_4$ and go to step 2.
6. Output D obtained by taking the square root of every element of $\hat{Q}_4$.

In other words, the step of denoising S160 may include: defining a second stopping criterion; storing a current testing matrix Q representing the distance matrix S164; making Q symmetric S182 by summing $\hat{Q}$ with its transpose and dividing the summed result by two; setting the diagonal elements of $\hat{Q}$ to zero S184; setting all the negative elements of $\hat{Q}$ to zero S186; computing a singular value decomposition of $\hat{Q}$ and setting all the singular values of $\hat{Q}$ to zero except the four largest ones S188; determining a test value to compare to a second stopping criterion S168; comparing the test value to the second stopping criterion S172; repeating the storing and various modifying steps S174 until the norm of the difference satisfies the second stopping criterion; deriving a denoised distance matrix from the final modified $\hat{Q}$ matrix after the second stopping criterion is satisfied S176; and providing the denoised distance matrix as an output S178. The modifying steps may be performed in any suitable order. Or instance, the steps of computing a singular value decomposition of $\hat{Q}$ and setting all the singular values of $\hat{Q}$ to zero except the four largest values may be performed before the steps of setting the diagonal and negative elements of $\hat{Q}$ to zero.

Step S154 and S190, which includes modifying the estimated positions of the transducers $\hat{x}_i$ based on the modified distance matrix or denoised modified distance matrix, respectively, function to provide a modified estimate of the positions of the transducers, which may be useful for providing a comparative point to determine when to stop the iteration and/or for providing a calibration parameter. Modifying the estimated positions of the transducers preferably include using a multi-dimensional scaling (MDS) algorithm, but may include any optimization or other step for obtaining updated estimated positions of the transducers from the modified distance matrix or other data set. In a preferred embodiment, the transducers positions estimates $\hat{X}=[\hat{x}_0, \hat{x}_1, \ldots, \hat{x}_{N-1}]^T$ are computed using a MDS algorithm described below: (e.g., the MDS algorithm may be similar to that described in P. Drineas et al., "Distance matrix reconstruction from incomplete distance information for sensor network localization," 3rd Annual IEEE Communications Society on Sensor and Ad Hoc Communications and Networks, September 2006, pp. 536-544, which is incorporated in its entirety by this reference):

MDS Localization

Input: A distance matrix D.

Output: Modified position estimates $\hat{X}$.

Procedure:

1. Compute $\tau(Q)=-(\frac{1}{2})LQL$, where $L=I-(1/N)11^T$ and Q is obtained by squaring every element of D.

2. Compute $\tau_2(Q)$, the best rank two approximation to $\tau(Q)$ using its singular value decomposition, $\tau_2(Q)=U_2\Lambda_2^2 U_2^T$.

3. Compute $\hat{x}=U_2\Lambda_2$.

Figure 5:
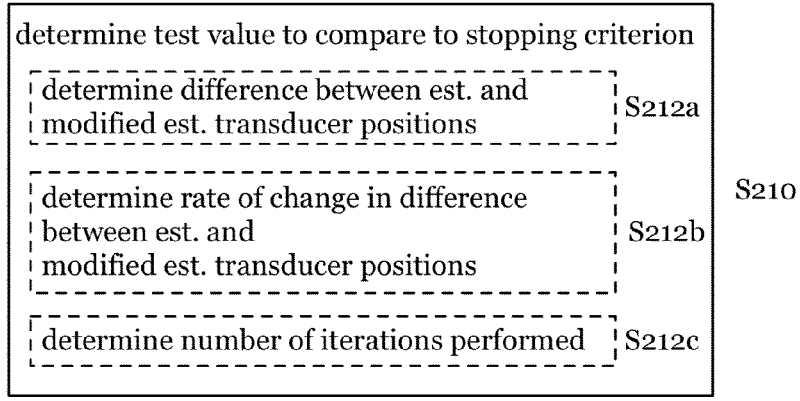
FIG. 5 is a detailed schematic of the step of determining a test value to compare to a first stopping criterion in the method of a preferred embodiment.

Step S210, which includes determining a test value to compare to a stopping criterion, functions to provide a measure for evaluating whether the estimated calibration parameters have a sufficient level of apparent accuracy. As shown in FIG. 5, step S210 may be one or more of several variations. In a first variation, step S210 includes determining the difference between the estimated and modified estimated positions of transducers S212a. Determining the difference between the estimated and modified estimated positions of transducers S212a preferably includes computing the norm of the difference between a vector of estimated positions of transducers and a vector of modified estimated positions of transducers. However, any other suitable indicator may be used to represent the difference between the estimated and modified estimated positions of transducers, such the mean of the difference between respective elements in the two vectors, or any suitable indicator. In a second variation, step S210 includes determining the rate of change in the difference S212b between the estimated and modified estimated positions of transducers, where the difference is calculated similarly to that in the first variation of step S210. In a third variation, step S210 includes determining the number of iterations of method 100 performed. However, step S210 may include any suitable steps for computing a test value for any suitable stopping criterion.

Step S220, which includes repeating at least steps S130 through S210 until the test value satisfies a stopping criterion, functions to iterate the modifications of the time delay measurement matrix and the distance matrix until particular estimated calibration parameters have a sufficient level of apparent accuracy. As shown in FIG. 1, step S220 includes comparing the test value to the stopping criterion S222. The stopping criterion may be a fixed numerical value or a dynamic numerical value (such as one that changes depending on the rate of change in the difference between multiple iterations). In a first case, if the test value is greater than the stopping criterion, at least a portion of the method, more preferably steps S120 through S210, is repeated using the modified estimated positions of transducers and modified time delay measurement data set as the initial values for the next iteration. In a second case, if the test value is less than the stopping criterion, then the iterations preferably stop and the modified estimated positions of transducers and modified time delay parameters may be considered sufficiently accurate. In a third case, if the test value is equal to the stopping criterion, the method may perform the action of the first or the second case.

The method may further include step S230, which includes providing an output of at least one of the estimated calibration parameters. Providing an output S190 may include displaying on a screen or printing one or more of the estimates.

The method may further include step S240, which includes saving at least one of the estimated calibration parameters. The estimates may be saved to a hard drive, on a removable storage device, a server, or any suitable storage system. For instance, one or more estimates obtained through the method may be stored for future use during an experimental run with the transducer array. As another example, the estimates may be stored for comparison to previous or future estimates obtained through the method or other means, such as for tracking changes in the estimated transducer positions or time delay parameters over time or comparing parameters corresponding to other propagation mediums.

In one preferred embodiment, the method for estimating speed of propagation $\hat{c}$ of an homogeneous medium and positions $\hat{x}_i$, emission delays $\hat{e}_i$ and reception delays $\hat{r}_i$ of transducers based on time delay measurements $\hat{m}_{i,j}$ between pairs of said transducers (i,j=0, 1, ..., N−1) includes the following steps:

1. building a measurement matrix comprising time delay measurements $\hat{m}_{i,j}$ between any pair of transducers, 2. removing rows and columns of the measurement matrix that correspond to faulty transducers, 3. defining a stopping criterion, 4. building a mask that sets missing entries in the measurement matrix to zero, 5. choosing initial positions $\hat{x}_i$ of the transducers, 6. storing the current positions, 7. building a matrix that contains the pairwise distances between the transducers, 8. applying the mask to the measurement matrix, 9. computing mean square optimal estimates of the propagation speed $\hat{c}$, the emission delays $\hat{e}_i$ and the reception delays $\hat{r}_i$ using the non-zero measurements $\hat{m}_{i,j}$, 10. computing interpolated values for the zero entries of the measurement matrix using the current speed of propagation estimate $\hat{c}$ and the distance matrix, 11. computing a new distance matrix by subtracting the estimated delays $\hat{e}_i$ and $\hat{r}_i$ to the measurement matrix and multiplying by the estimated speed of sound $\hat{c}$, 12. computing a denoised version of the distance matrix using an iterative algorithm, 13. updating the positions $\hat{x}_i$ of the transducers using a multi dimensional scaling algorithm on the denoised distance matrix, 14. computing the norm of the difference between the current positions and those stored in step 6, 15. repeating the method from step 6 if the norm of the difference is larger that the stopping criterion, and 16. choosing the current estimates of at least one of the calibration parameters of $\hat{c}$, $\hat{x}_i$, $\hat{e}_i$ and $\hat{r}_i$ as the output.

In a preferred embodiment, computing a denoised version of the distance matrix may include the steps of:

1. defining a second stopping criterion, 2. storing the current distance matrix $\hat{D}$, 3. making the distance matrix $\hat{D}$ symmetric by adding its transpose and dividing the result by two, 4. computing a singular value decomposition of the distance matrix $\hat{D}$, 5. setting all the singular values of the distance matrix $\hat{D}$ to zero except the four largest ones,
6. setting the diagonal elements of the distance matrix $\hat{D}$ to zero,
7. setting all the negative elements of the distance matrix $\hat{D}$ to zero,
8. computing the norm of the difference between the current distance matrix $\hat{D}$ and that stored in step 2 of computing a denoised version of the distance matrix,
9. repeating the method of computing a denoised version of the distance matrix from step 2 if the norm of the difference is larger that the second stopping criterion, and
10. choosing the current distance matrix $\hat{D}$ as the output.

In a preferred embodiment, a system 300 for calibration of a transducer array characterized by calibration parameters, based on time delay measurements between transducer pairs, includes: a plurality of transducers 310 that perform at least one of emitting and receiving a signal; a data controller 320 that forms a distance data set including pairwise distances between estimated positions of transducers and a time delay measurement data set including time delay measurements between transducer pairs, including non-faulty time delay measurements and any faulty time delay measurements; and estimation engine 330 that generates from the time delay measurement data set an estimate of at least one calibration parameter 312. The data controller 320 modifies the faulty time delay measurements in the time delay measurement data set and the estimated positions of transducers in the distance in the distance data set based on the estimated calibration parameters. The data controller 320 and estimation engine 330 preferably iteratively cooperate until a test value satisfies a stopping criterion. The test value may represent the difference between the estimated positions of transducers and final modified estimated positions of transducers, the rate of change of the difference between multiple iterations, the number of iterations performed up to that point, and/or any suitable test value. The system 300 preferably generates estimates of at least one of calibration parameters including: positions of transducers, emission delay, reception delay, and speed of signal propagation, but may additionally and/or alternatively generate estimates of any other suitable calibration parameter. The system may further include a signal processor 340 that denoises the modified distance data set with an iterative algorithm, preferably performing steps similar to step S160 in method 100, but alternatively any suitable denoising algorithm. In a preferred embodiment, the data controller and/or the estimation engine outputs (e.g., displaying or printing) or stores at least one of the estimated calibration parameters 312.

EXAMPLE

Figure 9:
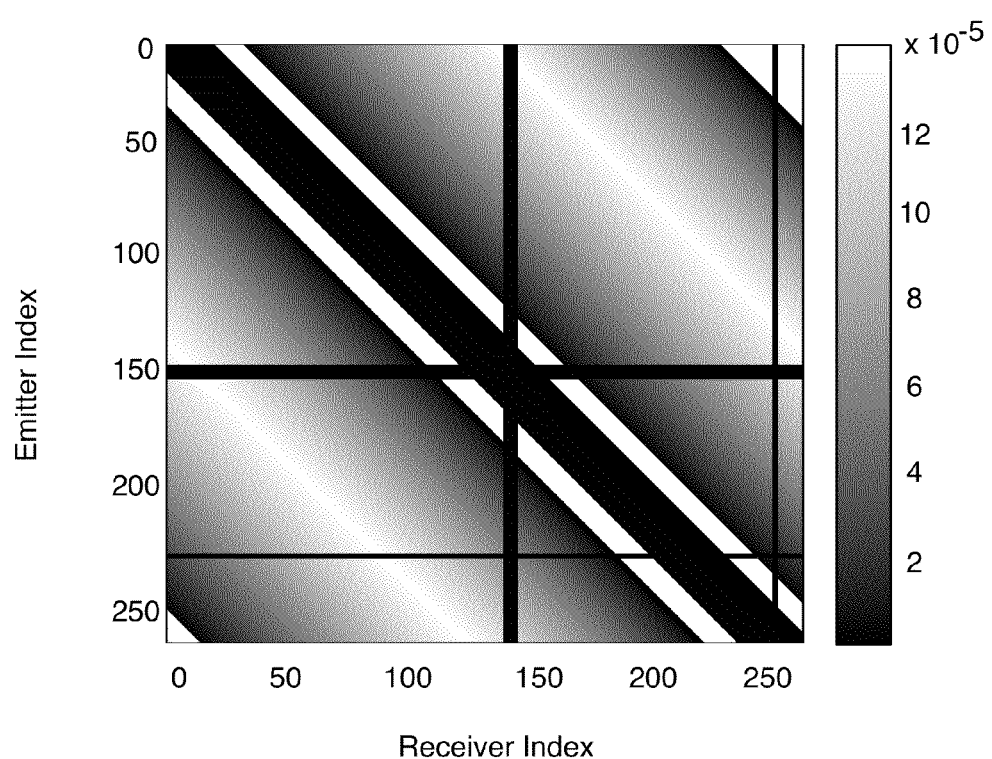
FIG. 9 is a measurement matrix obtained with a ring transducer with a plurality of transducer elements in an example embodiment of the method.

The calibration method may be applied to the calibration of a set of N=256 ultrasound transducers used in a clinical prototype for breast cancer detection. The transducers are initially assumed to be uniformly spaced with an angular separation a of 0.024 radians<a<0.025 radians on a ring of radius r=0.0999 meters. Furthermore, the overall initial emission/reception delay of each transducer pair is assumed to be a constant $\tau$. This amounts to set the matrices $K_e$ and $K_r$ in (4) as the all-one vector and choose e and r as the scalar $\tau/2$. Measurements are computed from a water shot of a patient using a time delay estimation method based on the arrival of the first peak of the transmitted signal. The obtained measurement matrix is depicted in FIG. 9.

Due to the directional response of the transducers, the signals transmitted between adjacent pairs of emitters and receivers have a low signal-to-noise ratio and the corresponding time delays cannot be computed. In this case, as shown in FIG. 9, the 20 first off-diagonal elements of the measurement matrix are missing. Moreover, the transducers 30, 96, 144 to 151, and 243 to 246 are considered as too noisy and are discarded.

Figure 10A:
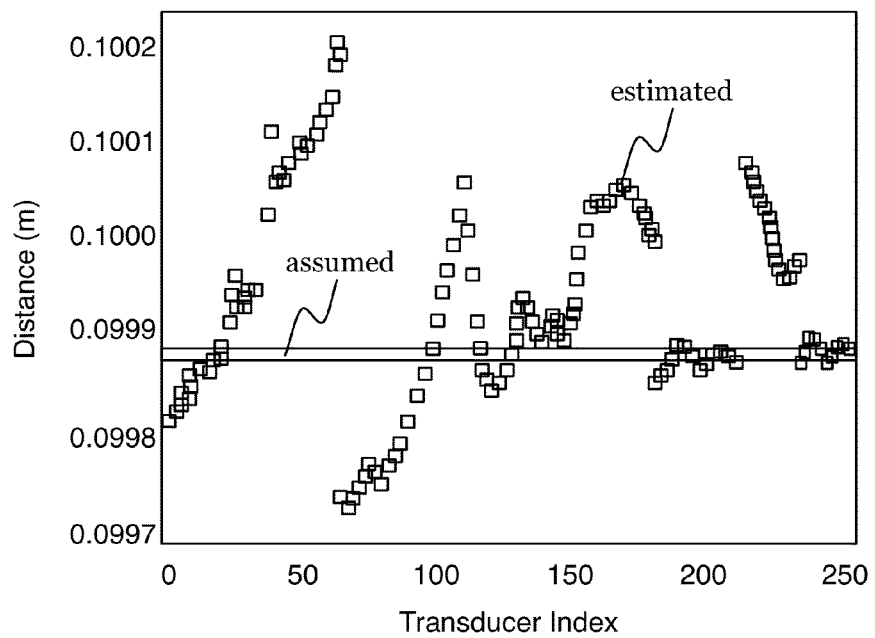
FIGS. 10A and 10B are plots illustrating the comparison between estimated transducer positions and assumed transducer positions, according to distance from the center of a transducer ring and angle between adjacent transducer elements, respectively, where the estimated transducer were obtained in an example embodiment of the method and the assumed transducer positions are based on known approximate geometry of the transducer ring.
Figure 10B:
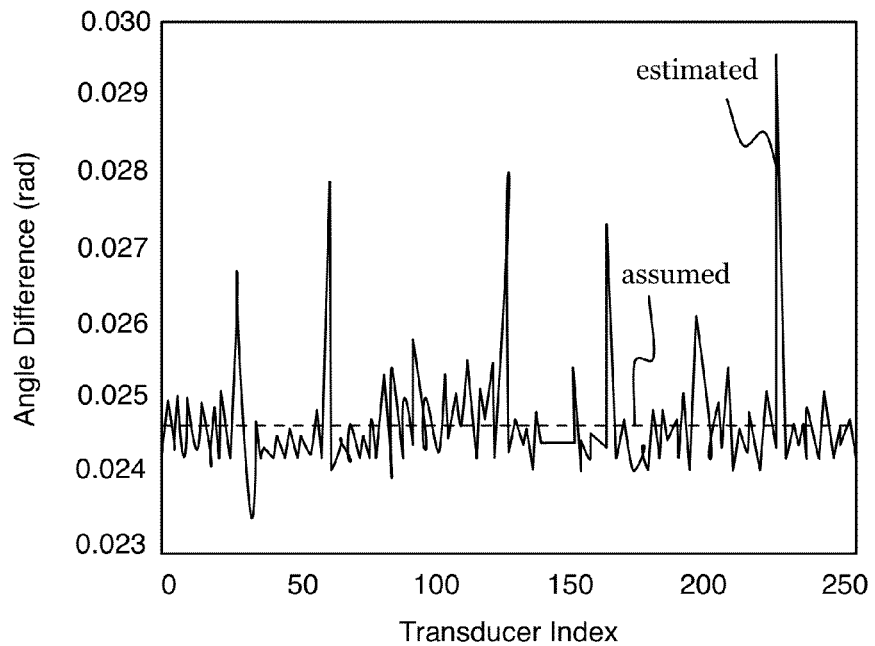

The algorithm was run on the time delay data including the measurement matrix. As shown in FIGS. 10A and 10B, the estimated positions differ from the assumed uniform ring geometry. In FIG. 10A, the distance of every element to the center of the array can be plotted, and the values can be clearly seen to depart from the assumed constant radius r=0.0999 meters. A block structure can also be observed that reflects the way the array was built, that is, by concatenating small line arrays. In FIG. 10B, the angle differences between two consecutive transducers can be plotted and compared to the uniform angular spacing 0.024 radians<a<0.025 radians of the assumed ring geometry. Here, significant differences can be observed every 32 elements, which probably correspond to consecutive transducers lying on two different line arrays. Note that the positions of the bad transducers have been linearly interpolated (in radius and angle) between the closest good transducers. For this water shot, the estimated sound speed is $\hat{c}$=1509.5 meters per second, and the delay of the transducers, including the systematic delay introduced by the time delay estimation method (i.e., the time to the first peak), is about 2.68 microseconds. The temperature of the water during the experiment is T=30.3740 degrees Celsius, which translates into a sound speed of c=1510.1 meters per second according to the formula $c=1405.3+4.624\,T-0.0383\,T^2$. Note that this formula for c is accurate for temperatures between 10 and 40 degrees Celsius. The water sound speed is thus estimated with high accuracy.

Figure 11A:
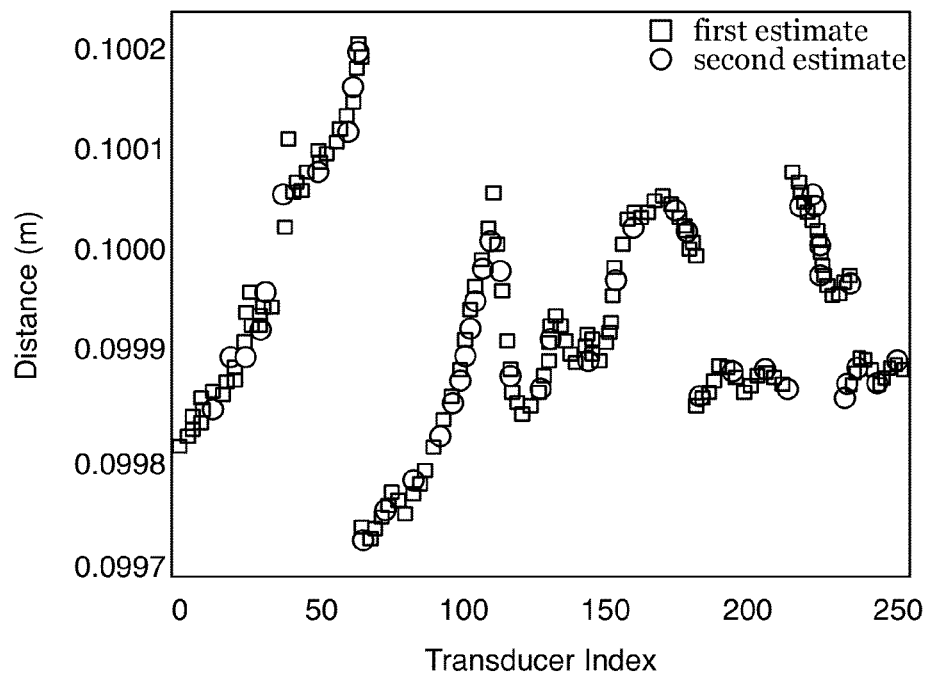
FIGS. 11A and 11B are plots illustrating the comparison between a first set of estimated transducer positions and a second set of estimated transducer positions, according to distance from the center of a transducer ring and angle between adjacent transducer elements, respectively, where the first and second sets of estimated transducer positions were obtained in first and second instances, respectively, of an example embodiment of the method.
Figure 11B:
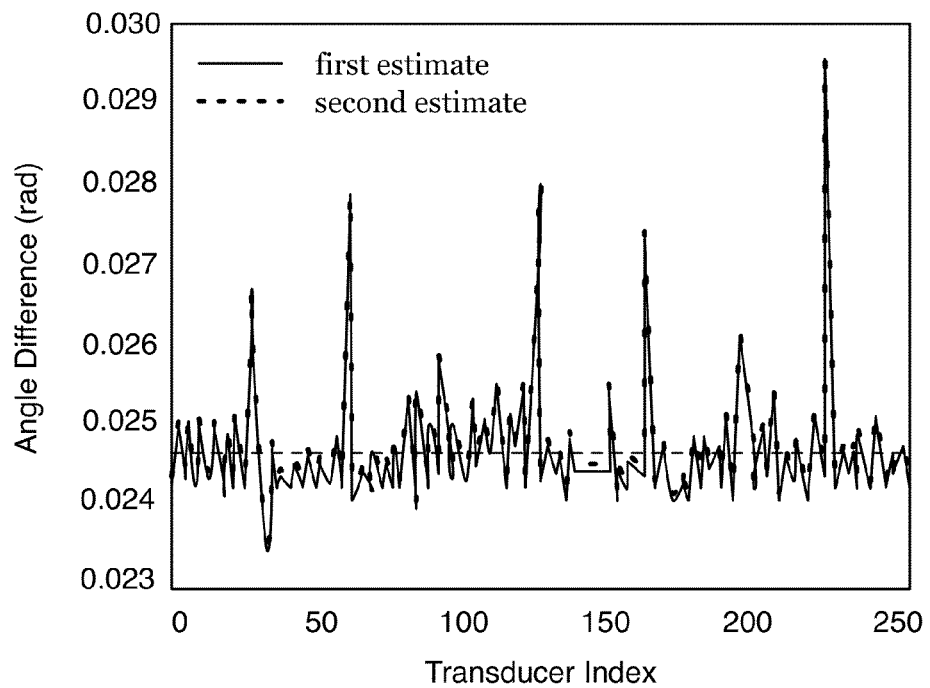

To check consistency of the calibration parameters, the calibration was performed again using a second water shot of the same prototype with another patient. In this case, the estimated sound speed is $\hat{c}$=1500.5 meters per second, and the delay is about 2.63 microseconds. The temperature of the water during experiment is T=26.6 degrees Celsius which corresponds to a sound speed of c=1500.9 meters per second. As shown in FIGS. 11A and 11B (distance from the center and angle between adjacent transducer elements, respectively), the estimates of the positions of the transducers using the first and second water shots show a good consistency between the two different calibrations, which suggest that the calibration parameters are well estimated and consistent between water shots.

As a person skilled in the art will recognize from the previous detailed description and from the figures and claims, modifications and changes can be made to the preferred embodiments of the invention without departing from the scope of this invention defined in the following claims.

We claim:
1. An iterative method for calibrating a transducer array characterized by calibration parameters, based on time delay measurements between transducer pairs, comprising the steps of:
   a. receiving an estimate of the positions of the transducers;
   b. at a data controller, forming a time delay measurement data set that includes time delay measurements between transducer pairs, including non-faulty time delay measurements and any faulty time delay measurements;
   c. at an estimation engine, generating from the time delay measurement data set an estimate of at least one calibration parameter;

d. at the data controller, modifying the time delay measurement data set including the faulty time delay measurements, based on the estimated of at least one calibration parameters;

e. at the data controller, modifying the estimated positions of the transducers based on the estimated of at least one calibration parameters;

f. determining a test value to compare to a stopping criterion; and g. repeating steps (c) through (f) until the test value satisfies the stopping criterion.

2. The method of claim 1, wherein:

receiving an estimate of the positions of the transducers includes creating a distance matrix of estimated pairwise distances between estimated positions of transducers; and modifying the estimated positions of the transducers includes modifying the distance matrix with modified estimated pairwise distances between modified estimated positions of transducers, wherein the modified estimated positions of transducers are based on the estimated of at least one calibration parameters.

3. The method of claim 2, further comprising denoising the modified distance data set before modifying the estimated positions of the transducers, and wherein modifying the estimated positions of the transducers includes modifying the estimated positions of the transducers based on the denoised modified distance matrix.

4. The method of claim 3 denoising a testing matrix with an iterative algorithm, wherein the testing matrix represents elements in the modified distance data set.

5. The method of claim 4, wherein denoising the testing matrix includes storing the modified distance matrix as the testing matrix and iteratively reinforcing at least one desired property of the testing matrix.

6. The method of claim 5, wherein iteratively reinforcing at least one desired property includes reinforcing at least one property selected from the group consisting of: matrix symmetry, zero diagonal elements, non-negative elements, and rank equal to or less than four.

7. The method of claim 2, wherein modifying the estimated positions of the transducers includes updating the estimated positions using a multi-dimensional scaling algorithm.

8. The method of claim 4, wherein denoising the testing matrix includes storing a time-of-flight matrix as the testing matrix and iteratively reinforcing at least one desired property of the testing matrix, wherein the time-of-flight matrix is defined as the distance matrix divided by an estimated speed of signal propagation.

9. The method of claim 5, wherein iteratively reinforcing at least one desired property of the testing matrix includes:

storing an initial testing matrix that includes the square of every element in the modified distance matrix;

manipulating the initial testing matrix to possess at least one desired property;

determining a second test value to compare to a second stopping criterion; and repeating the steps of storing, manipulating, and comparing determining until the second test value satisfies the second stopping criterion, wherein in each iteration the repeated step of storing an initial testing matrix includes storing an initial testing matrix that is equivalent to the manipulated testing matrix of the previous iteration.

10. The method of claim 9, wherein determining a second test value includes determining the difference between the initial testing matrix and the manipulated testing matrix.

11. The method of claim 1, wherein forming a time delay measurement data set includes flagging faulty time delay measurements.

12. The method of claim 11, wherein forming a time delay measurement data set includes forming a time delay measurement matrix of time delay measurements between transducer pairs, including any faulty time delay measurements.

13. The method of claim 12, wherein flagging faulty time delay measurements includes applying a mask to the time delay measurement matrix that sets the faulty time delay measurements to zero.

14. The method of claim 1, wherein generating an estimate of at least one calibration parameter includes optimizing values for at least one time delay parameter using the non-faulty time delay measurements.

15. The method of claim 14, wherein optimizing values for at least one time delay parameter includes computing mean square optimal estimates of at least one calibration parameter.

16. The method of claim 14, wherein generating an estimate of at least one calibration parameter includes generating an updated estimate of at least one calibration parameter selected from the group consisting of: speed of signal propagation, emission delay, and reception delay.

17. The method of claim 1, wherein receiving an estimate of the positions of the transducers includes estimating the pairwise Euclidean distances between estimated positions of transducers.

18. The method of claim 17, wherein estimating the Euclidean distances between transducer pairs includes creating a distance matrix of estimated pairwise distances between estimated positions of transducers.

19. The method of claim 1, wherein modifying the time delay measurement data set includes interpolating updated values for the faulty time delay measurements using the estimated of at least one calibration parameters and modifying the faulty time delay measurements to the interpolated values.

20. The method of claim 19, wherein interpolating updated values includes interpolating updated values based on the relative positions of the transducers and an estimated speed of signal propagation.

21. The method of claim 1, wherein modifying the estimated relative positions of the transducers includes modifying the estimated relative positions based on estimated values of emission delay and reception delay.

22. The method of claim 21, wherein modifying the estimated relative positions of the transducers includes subtracting estimated emission and reception delay values from the time delay measurement data set, and multiplying the result of the subtraction by an estimated speed of signal propagation.

23. The method of claim 1, wherein determining a test value includes determining the difference between the estimated positions of transducers and the modified estimated positions of transducers.

24. The method of claim 23, wherein determining the difference between the estimated positions of transducers and the modified estimated positions of transducers includes computing the norm of the difference between the estimated positions of transducers and the modified estimated positions of transducers.

25. The method of claim 1, further comprising the step of providing an output of at least one calibration parameter.

26. The method of claim 1, further comprising the step of storing an output of at least one calibration parameter.

27. An iterative method for calibrating a transducer array characterized by calibration parameters, based on time delay measurements between transducer pairs, comprising the steps of:
   a. at a data controller, creating a distance data set that includes pairwise distances between estimated positions of transducer;
   b. at the data controller, forming a time delay measurement data set that includes time delay measurements between transducer pairs;
   c. at an estimation engine, generating from the time delay measurement data set an estimate of at least one calibration parameter;
   d. at the data controller, modifying the time delay measurement data set and the distance data set based on the estimated of at least one calibration parameters;
   e. at a signal processor, denoising the modified distance data set with an iterative algorithm;
   f. updating the estimated positions of transducers based on the denoised modified distance data set; and
   g. repeating steps (c) through (f) until a test value satisfies a stopping criterion.

28. The method of claim 27, wherein iteratively reinforcing at least one desired property includes
   storing an initial testing matrix that represents elements in the modified distance data set;
   manipulating the initial testing matrix to possess at least one desired property;
   determining a second test value; and
   repeating the steps of storing, manipulating, and determining to achieve a final manipulated testing matrix until the second test value satisfies a second stopping criterion, wherein in each iteration the repeated step of storing an initial testing matrix includes storing an initial testing matrix that is equivalent to the manipulated testing matrix of the previous iteration; and
   deriving a denoised modified distance data set from the final manipulated testing matrix.

29. The method of claim 28, wherein determining a second test value includes determining the difference between the manipulated testing matrix to the initial testing matrix.

30. The method of claim 28, wherein manipulating the initial testing matrix includes making the initial testing matrix symmetric, including summing the initial testing matrix and the transpose of the initial testing matrix, and dividing the summed result by two.

31. The method of claim 28, wherein manipulating the initial testing matrix includes at least one of the following steps:
   setting the diagonal elements of the symmetric testing matrix to zero;
   setting the negative elements of the symmetric testing matrix to zero; and
   setting all but the four largest singular values of the symmetric testing matrix to zero.

32. The method of claim 27, further comprising storing a testing matrix that represents elements in the modified distance data set, wherein denoising the modified distance data set includes iteratively reinforcing at least one desired property of the testing matrix.

33. The method of claim 27, further comprising determining a test value representing the difference between the estimated positions of transducer pairs and updated estimated positions of transducers.

34. A system for calibration of a transducer array characterized by calibration parameters, based on time delay measurements between transducer pairs, comprising:
   a plurality of transducers that perform at least one of emitting and receiving a signal;
   a data controller that forms a distance data set including pairwise distances between estimated positions of transducers and a time delay measurement data set including time delay measurements between transducer pairs, including non-faulty time delay measurements and any faulty time delay measurements;
   an estimation engine that generates from the time delay measurement data set an estimate of at least one calibration parameter from the group consisting of an emission delay, a reception delay, and a speed of signal propagation;
   wherein the data controller modifies the faulty time delay measurements in the time delay measurement data set and the estimated positions of transducers in the distance data set based on the estimated calibration parameter;
   wherein the data controller and estimation engine iteratively cooperate until a test value satisfies a stopping criterion.

35. The system of claim 34, wherein the test value represents the difference between the estimated positions of the transducers and a final set of modified estimated positions of transducers.

36. The system of claim 34, wherein at least one of the data controller and estimation engine outputs at least one estimated calibration parameter.

37. The system of claim 34, further comprising a signal processor that denoises the modified distance data set with an iterative algorithm.

38. An iterative method for calibrating a transducer array characterized by calibration parameters, based on time delay measurements between transducer pairs, comprising the steps of:
   at a data controller, forming a time delay measurement data set that includes time delay measurements between transducer pairs, including non-faulty time delay measurements and any faulty time delay measurements;
   at an estimation engine, generating from the non-faulty time delay measurement data set an estimate of at least one calibration parameter;
   at the data controller, modifying the faulty time delay measurements in the time delay measurement data set based on the estimated of at least one calibration parameters; and
   repeating the steps of generating an estimate of at least one time delay parameter and modifying the faulty time delay measurements using an iterative masking algorithm until a stopping criterion is satisfied.

* * * * *